(12) United States Patent
Haberer

(10) Patent No.: US 7,091,478 B2
(45) Date of Patent: Aug. 15, 2006

(54) METHOD AND DEVICE FOR CONTROLLING A BEAM EXTRACTION RASTER SCAN IRRADIATION DEVICE FOR HEAVY IONS OR PROTONS

(75) Inventor: Thomas Haberer, Frankfurt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 10/502,860

(22) PCT Filed: Dec. 13, 2002

(86) PCT No.: PCT/EP02/14256

§ 371 (c)(1),
(2), (4) Date: Dec. 29, 2004

(87) PCT Pub. No.: WO03/069634

PCT Pub. Date: Aug. 21, 2003

(65) Prior Publication Data

US 2005/0116175 A1 Jun. 2, 2005

(30) Foreign Application Priority Data

Feb. 12, 2002 (DE) .............................. 102 05 949

(51) Int. Cl.
*G21G 5/00* (2006.01)

(52) U.S. Cl. ................... 250/283; 250/492.2; 250/397; 250/396 R; 250/396 ML; 315/505

(58) Field of Classification Search .................... None
See application file for complete search history.

(56) References Cited

U.S. PATENT DOCUMENTS

| 5,017,789 A | | 5/1991 | Young et al. |
| 5,895,926 A | * | 4/1999 | Britton et al. ............ 250/492.3 |
| 6,683,318 B1 | * | 1/2004 | Haberer et al. .......... 250/492.3 |
| 6,809,325 B1 | * | 10/2004 | Dahl et al. ............... 250/492.3 |

FOREIGN PATENT DOCUMENTS

| EP | 0 251 407 A | 1/1988 |
| EP | 0 986 070 A | 3/2000 |
| EP | 1 045 399 A | 10/2000 |

* cited by examiner

*Primary Examiner*—John R. Lee
*Assistant Examiner*—Zia R. Hashmi
(74) *Attorney, Agent, or Firm*—Frommer Lawrence & Haug LLP; Ronald R. Santucci

(57) ABSTRACT

The invention relates to a method and to a device for controlling a beam extraction irradiation device for heavy ions operating according to the raster scan technique, wherein the beam energy, beam focusing and beam intensity are adjusted for every accelerator cycle. By adjusting the beam extraction duration for every accelerator cycle, considerable savings of time are achieved.

13 Claims, 3 Drawing Sheets

METHOD AND DEVICE FOR CONTROLLING A BEAM EXTRACTION RASTER SCAN IRRADIATION DEVICE FOR HEAVY IONS OR PROTONS

This application is a 371 of PCT/EP02/14256 filed on Dec. 13, 2002, published on Aug. 21, 2003 under publication number WO 03/069634 and which claims priority benefits from German patent application number DE 102 05 949.7 filed Feb. 12, 2002.

The present invention relates to a method and to a device for controlling a beam extraction irradiation device for heavy ions or protons operating according to the raster scan technique, wherein the beam energy, beam focusing and beam intensity are adjusted for every accelerator cycle.

Such a method and such a device are already known from the prior art, for example, from EP 1 045 399 A1, which is concerned with the increase in the geometrical precision of the dose application and with independence from variations in beam position. As a result, it was possible to achieve a dose distribution resulting from the total irradiation that differed on average by less than 5% from the planned dose distribution.

Figure 3:
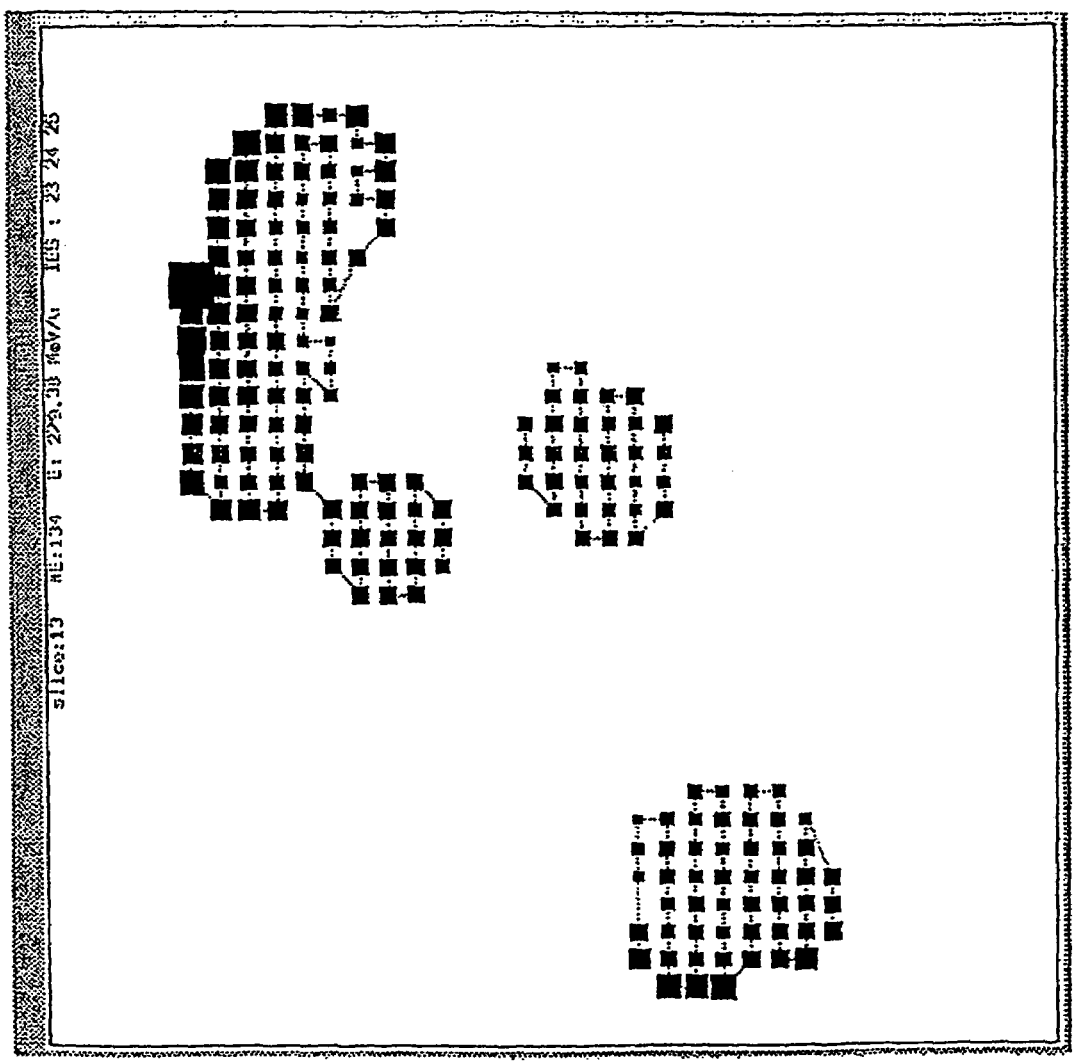

A basic explanation of the intensity-controlled raster scan technique is given in the article "Magnetic scanning system for heavy ion therapy" by Th. Haberer, W. Becher, D. Schardt and G. Kraft, Nuclear Instruments and Methods in Physics Research A330, pages 296–305, 1993. Using the raster scan technique, the therapeutically highly effective ions can be concentrated to the treatment volume defined by the doctor, which permits an optimum therapy result. The raster scan technique consists here of a combination of transversal diversion of a focussed particle beam in rapid dipole magnets with variation of the beam energy in the accelerator to determine the particle range. The virtual segmentation of the treatment volume within the limits of a radiation treatment plan is illustrated in FIG. 3. A series of slices of constant particle energy (isoenergy slices IES) is prepared. The isoenergy slices are in turn segmented into a raster of beam positions and for each individual beam position a particle density is optimised.

To irradiate the individual isoenergy slices of a radiation treatment plan, at present an accelerator cycle is determined with the three adjustable parameters beam energy, beam focusing and beam intensity. The cycle duration and hence the duration of the beam extraction is set to a fixed value. This procedure involves disadvantages, since isoenergy slices cannot necessarily be processed in this way with one accelerator cycle, on the contrary, a beam extraction time longer by up to a factor 10 would be needed. The acceleration and deceleration times associated with the use of several accelerator cycles, as well as the times required for accelerator preparation, create an additional time outlay, which is of the order of magnitude of the extraction time.

Further time losses result from the need for so-called conditioning cycles, that is, accelerator cycles without beam extraction, which have to run in order to create defined field conditions in the magnets of the accelerator and the beam guides, without an irradiation being able to be carried out.

Further irradiation dead times arise as a result of the fact that albeit when the irradiation target (all irradiation positions could be irradiated within an isoenergy slice) or a so-called interlock situation is reached, the irradiation, that is, the beam extraction and the beam transport, is interrupted, according to the methods currently in use this nevertheless does not lead to interruption of the accelerator cycle, that is, this continues without beam extraction.

Another need to interrupt the irradiation arises whenever the tissue to be irradiated has a complex geometry, is inhomogeneous in density and thus gives rise to radiation treatment plans with non-contiguous areas that nevertheless have to be irradiated with the same beam parameters. Other radiation treatment plans with non-contiguous areas in turn have to be irradiated with the same beam energy but not with the same settings for focusing and intensity. According to the current state of the art, however, interruption of the beam leads to loss of the extraction facility within the ongoing accelerator cycle, that is, a new accelerator cycle has to be requested. Also, it is not possible to re-establish the beam extraction within an accelerator cycle, nor to alter the focusing state and/or the beam intensity within an accelerator cycle.

The invention is based on the problem of configuring a control means of an irradiation device operating according to the raster scan technique in such a way that a high efficiency factor combined with reduced irradiation duration is achieved.

That problem is solved in accordance with the invention in the case of a method and a device by the features of claims 1 and 8 respectively. Advantageous developments are the subject matter of the subsidiary claims.

According to the invention a method is therefore proposed for controlling a beam extraction irradiation device for heavy ions or protons operating according to the raster scan technique, in which the beam energy, beam focusing and beam intensity are adjusted for every accelerator cycle. At the same time, the beam extraction is also determined for every accelerator cycle.

The invention is thus applied in accelerators that run in cycles. Advantageously, in the method according to the invention the duration of the beam extraction is adjusted for every accelerator cycle. The variable beam extraction duration (flat-top time) enables the irradiation dead times arising as a consequence of new accelerator cycle requests to be appreciably reduced, thus producing substantial savings of time and a markedly higher patient turnover.

If the inventive method is to be used with a DC (direct current) machine, for instance with a cyclotron, creation of the time structure of the beam (ON/OFF) and the necessary flexibility of the beam parameters (intensity, focus) have to be effected in a different way.

A further measure for more flexible control of the irradiation procedure arises from by the fact that the particle charge can also be varied from accelerator cycle to accelerator cycle. It is therefore possible to achieve a more effective protection against radiation.

According to an advantageous variant of the method according to the invention, the beam extraction can be interrupted and reestablished again during an accelerator cycle. This variant is especially suitable for irradiation of non-contiguous areas with a constant beam energy, possibly also constant beam focusing and beam intensity.

A flexible irradiation treatment is provided when the beam focusing and/or the beam intensity is altered during an accelerator cycle. In this way, within an accelerator cycle it is possible to operate, for example, with the same beam energy but with a modified therapy beam.

The measures listed above for determining the beam extraction, such as variable and interruptible beam extraction, alterable focus and intensity, produce highly flexible beam request mechanisms. The irradiation duration can thus be dramatically reduced.

The measure of a field control of the accelerator magnet supply and beam guidance enables the conditioning cycles mentioned in the introduction to be largely or completely omitted, since the extracted treatment beam can be made available in a stable and precise form.

Application of the above-mentioned measures according to the invention, alone or in combination, enables the irradiation duration to be considerably reduced. A calculation of the anticipated reduction in irradiation time in the case of a combination of all measures has, for radiation treatment plans already carried out, produced a reduction in the mean irradiation duration to about a third of the time previously required.

A device according to the invention for controlling a beam extraction irradiation device for heavy ions operating according to the raster scan technique, especially for carrying out the method according to the invention, comprises an adjusting device for the beam extraction duration of each accelerator cycle. Preferably, it comprises a device for interrupting and re-establishing the extraction beam within an accelerator cycle. For that purpose, according to a preferred exemplary embodiment of the invention extraction and/or injection kickers, that is, fast magnets, are provided. Alternatively, a device for KO-extraction of the extraction beam can be provided.

According to another embodiment of the inventive device, an adjusting device is provided for modifying the focusing and/or the intensity of the extraction beam during an accelerator cycle.

Figure 1:
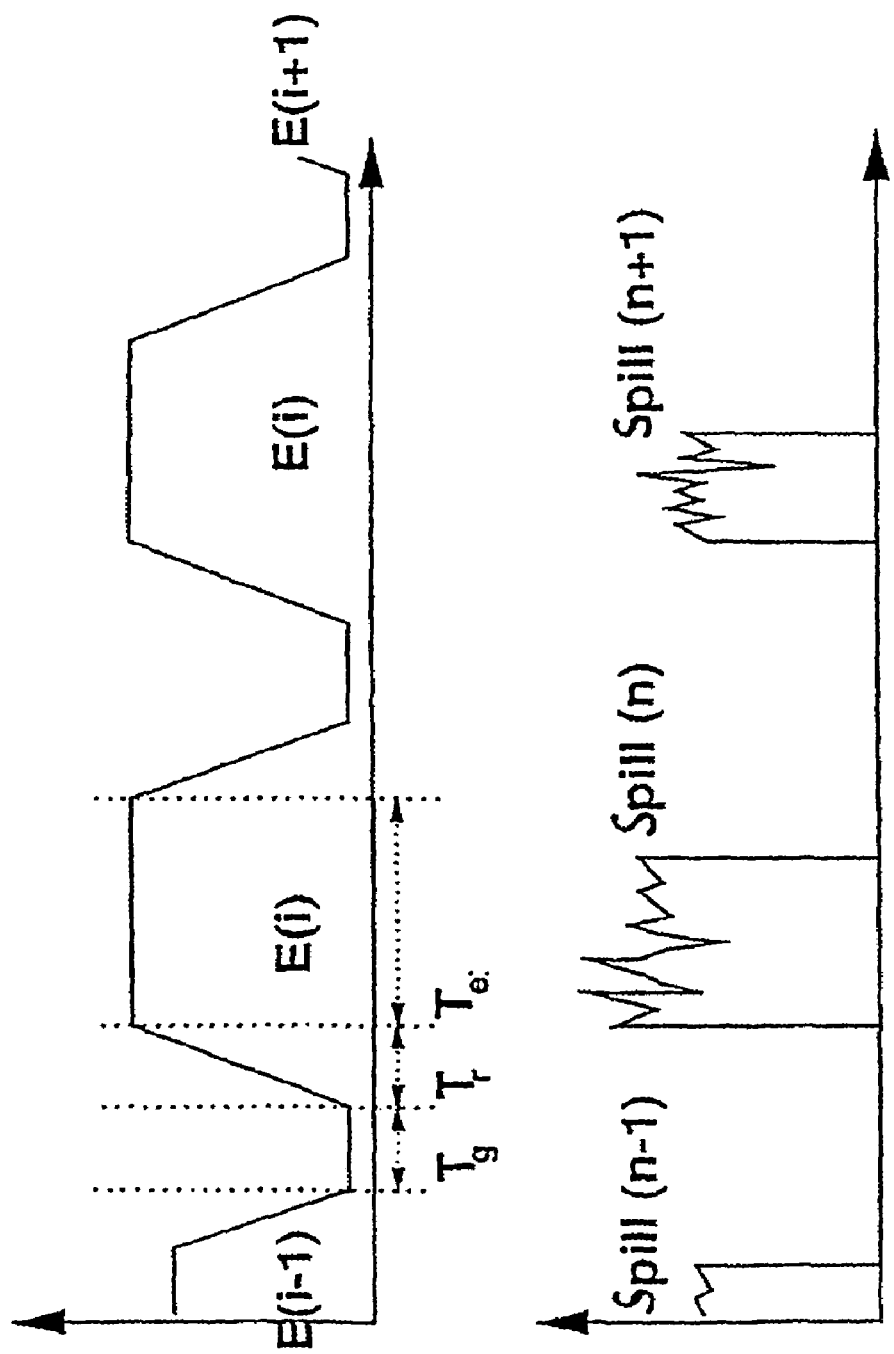
Figure 2:
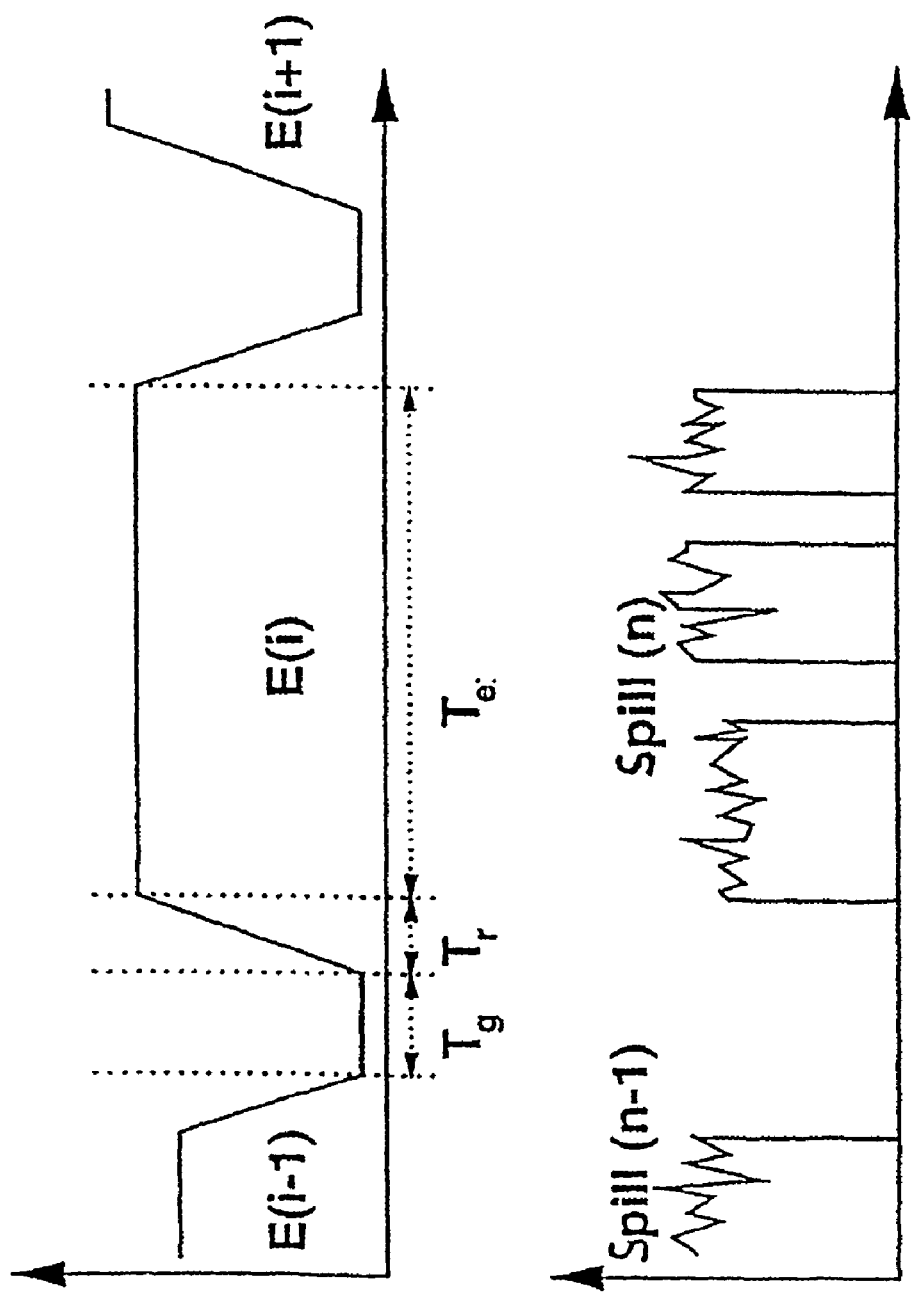

The invention is explained in the following with reference to the drawings, in which:

FIG. 1 is an illustration of a radiation treatment plan according to the invention, which contains non-contiguous areas that are to be irradiated with the same beam parameters, FIG. 2 shows a radiation treatment plan according to the prior art, which contains non-contiguous areas that are to be irradiated with the same beam parameters, and FIG. 3 is an illustration of a virtual segmenting of the treatment volume performed within the scope of a radiation treatment planning with a series of isoenergy slices (IES).

The radiation treatment plans illustrated in FIGS. 1 and 2 show in the upper part the synchrotron dipole field, time being plotted on the abscissa and energy on the ordinate. The lower diagram in each case shows the intensity of the extraction beam, intensity again being plotted against the treatment time.

Whereas according to the conventional method shown in FIG. 2 different particle pulses (spills) occur, this leads to a longer time duration $T_e$, during which isolated isoenergy slices are to be irradiated, that is, per area a separate particle pulse (spill) occurs for an extraction duration.

The illustration of FIG. 1 shows clearly the time gain that can be achieved by the invention. It was possible to reduce the particle pulses by being able with one beam extraction to achieve masking of different areas by beam interruption. In the present example, instead of three particle pulses a single particle pulse therefore occurs, with fewer dead times. The illustration of FIG. 1 is not an empirically obtained illustration but is based on the analysis of 46 radiation treatment plans performed in the year 2000. The decrease in the mean irradiation duration produced a reduction from 251 to 87 seconds, virtually one third of the time.

The invention claimed is:

1. A method for controlling a beam extraction irradiation device for heavy ions or protons operating according to the raster scan technique, in which the beam energy, beam focusing and beam intensity are adjusted for every accelerator cycle, wherein the beam extraction is determined for every accelerator cycle.

2. A method according to claim 1, wherein the duration of the beam extraction is adjusted for every accelerator cycle.

3. A method according to claim 1, wherein the particle charge of the extraction beam is adjusted for every accelerator cycle.

4. A method according to claim 1, wherein the beam extraction is interrupted and re-established during an accelerator cycle.

5. A method according to claim 1, wherein the beam focusing is altered during an accelerator cycle.

6. A method according to claim 1, wherein the beam intensity is altered during an accelerator cycle.

7. A method according to claim 1, wherein a field control of the accelerator magnet supply and beam guidance is carried out.

8. A method according to claim 1, wherein the accelerator cycle is terminated on request.

9. A device for controlling a beam extraction irradiation device for heavy ions or protons operating according to the raster scan technique, especially for carrying out the method according to claim 1, wherein an adjusting device is provided for the beam extraction duration of every accelerator cycle.

10. A device according to claim 9, wherein a device for interrupting and re-establishing the extraction beam within an accelerator cycle is provided.

11. A device according to claim 10, wherein extraction and/or injection kickers are provided.

12. A device according to claim 10, wherein a device for KO-extraction of the extraction beam is provided.

13. A device according to claim 1, wherein an adjusting device is provided for modifying focusing and/or intensity of the extraction beam during an accelerator cycle.

* * * * *